US012758438B2

(12) United States Patent
Choi

(10) Patent No.: US 12,758,438 B2
(45) Date of Patent: Oct. 13, 2026

(54) DEVICE FOR DETECTING A MEDICAL CONDITION OF A SUBJECT AND METHOD FOR MANUFACTURING THEREOF

(71) Applicant: Pui Wah Choi, Hong Kong (HK)

(72) Inventor: Pui Wah Choi, Hong Kong (HK)

(*) Notice: Subject to any disclaimer, the term of this patent is extended or adjusted under 35 U.S.C. 154(b) by 545 days.

(21) Appl. No.: 17/802,749

(22) PCT Filed: Feb. 26, 2021

(86) PCT No.: PCT/CN2021/078069
§ 371 (c)(1),
(2) Date: Aug. 26, 2022

(87) PCT Pub. No.: WO2021/170075
PCT Pub. Date: Sep. 2, 2021

(65) Prior Publication Data

US 2023/0110577 A1 Apr. 13, 2023

Related U.S. Application Data

(60) Provisional application No. 62/982,258, filed on Feb. 27, 2020.

(51) Int. Cl.
*A61F 13/84* (2006.01)
*A61F 13/15* (2006.01)
(Continued)

(52) U.S. Cl.
CPC ........ *A61F 13/84* (2013.01); *A61F 13/15577* (2013.01); *D04H 1/02* (2013.01); *D04H 1/55* (2013.01); *A61F 2013/8473* (2013.01)

(58) Field of Classification Search
CPC ................ A61F 13/84; A61F 13/15577; A61F 2013/8473; D04H 1/02; D04H 1/55
See application file for complete search history.

(56) References Cited

U.S. PATENT DOCUMENTS

| | | | | |
|---|---|---|---|---|
| 2005/0215924 A1* | 9/2005 | Kao | .................. | A61B 10/0045 604/385.01 |
| 2008/0195068 A1* | 8/2008 | Kao | .................. | A61F 13/47218 604/385.01 |

(Continued)

FOREIGN PATENT DOCUMENTS

| | | |
|---|---|---|
| CN | 1728950 A | 2/2006 |
| CN | 104869968 A | 8/2015 |

(Continued)

OTHER PUBLICATIONS

Int. Search Report & Opinion, PCT/CN2021/078069, Apr. 26, 2021, mailed May 26, 2021.

(Continued)

*Primary Examiner* — Rebecca E Eisenberg
*Assistant Examiner* — Kate Elizabeth Strachan

(57) ABSTRACT

The present invention relates to a device for detecting a medical condition of a subject from a menstrual blood collected from said subject. The device comprises a sampling member comprising one or more polymeric materials, the sampling member, when arranged to be in contact with the menstrual blood, collects constituent biomolecules of the menstrual blood at the polymeric materials; and a positioning member comprising an absorbing material, the positioning member being configured to support the sampling member; wherein the positioning member is releasably attachable to a sanitary product wearable by the subject.

16 Claims, 16 Drawing Sheets

(51) Int. Cl.
*D04H 1/02* (2006.01)
*D04H 1/55* (2012.01)

(56) References Cited

U.S. PATENT DOCUMENTS

| | | | | |
|---|---|---|---|---|
| 2008/0269706 | A1* | 10/2008 | Long | A61F 13/505 600/300 |
| 2013/0331666 | A1* | 12/2013 | Miller | A61F 13/42 29/428 |
| 2015/0051510 | A1* | 2/2015 | Husmark | G01N 33/493 600/573 |
| 2017/0112685 | A1* | 4/2017 | Rasmussen | A61F 13/53 |

FOREIGN PATENT DOCUMENTS

| | | |
|---|---|---|
| CN | 106999164 A | 8/2017 |
| CN | 110013383 A | 7/2019 |
| DE | 20200700596241 | 9/2007 |

OTHER PUBLICATIONS

Prestrelski, S.J. et al., "1. Dehydration-induced conformational transitions in proteins and theri inhibition by stabilizers", Biophys J, 1993. 65(2): p. 661-671.
Carpenter, J.F. et al., "Comparison of Solute-Induced Portein Stabilization in Aqueous Solution and in the Frozen and Draied States" Journal of Dairy Science, 1990. 73(12): p. 3627-3636.
Wong, S.C.C. et al., "Menstrual Blood Human Papillomavirus DNA and TAP1 Gene Polymorphisms as Potential Biomarkers for Screening and Monitoring of Cervical Squamous Intraepithelial Lesion", J. Infect. Dis., 2018. 218(11): p. 1739-1745.
Wong, S.C. et al., "Human papillomavirus DNA detection in menstrual blood from patients with cervical intraepithelial neoplasia and condyloma acuminatum", J. Clin. Microbiol. 48(3): p. 709-713.
Chaisomchit, S. et al., "Stability of genomic DNA in dried blood spots stored on filter paper", Southeast Asian J. Trop. Med. Public Health, 2005. 36(1): p. 270-273.
Aitken, S.C. et al., "Stability of HIV-1 Nucleic Acids in Dried Blook Spot Samples for HIV-1 Drug Resistance Genotyping", PLoS One, 2015. 10(7): p. e0131541.
Wolfrum, S.G. et al., "Evaluation of dry and wet transport of at-home self-collected vaginal swabs for human papillomavirus testing"J. Med. Microbiol., 2012. 61(Pt 11): p. 1538-1545.
Basinska, T., "Hydrophilic Core-Shell Mircrospheres a Suitable Support for Controlled Attachment of Proteins and Biomedical Diagnostics", Macromol. Biosci., 2005. 5(12): p. 1145-1168.
Terao, K., "Encyclopedia of Polymeric Nanomaterials"S. Kobayashi et al. editors. 2021, Springer Berlin Heidelberg: Berlin, Heidelberg. p. 1-6.
Wisniewska, M. et al., "Comparison of adsorption affinity of polyacrylic acid for surfaces of mixed silica-alumina"Colloid and Polymer Science, 2014. 292(3): p. 699-705.
Tavakoli, J. et al., "Hydrogel Based Sensors for Biomedical Applications an Updated Review", Polymers, 2017. 9(8): p. 364.
Smith, C.B. et al., "Baterial flora of the vagina during the menstrual cycle findings in users of tampons, napkins, and sea sponges", Ann. Intern. Med., 1982. 96(6 Pt. 2): p. 948-951.
Eschenback, D.A. et al., "Influence of the Normal Menstrual Cycle on Vaginal Tissue, Discharge, and Microflora", Clinical Infectious Diseases, 2000. 30(6): p. 901-907.
Kalia, N. et al., "Microbiota in vaginal health and pathogenesis of recurrent vulvovaginal infections a critical review", Ann. Clin. Microbiol. Antimicrob., 2020. 19(1): p. 5.
Abdallah, A. et al., "Gastrointestinal Interaction between Dietary Amino Acids and Gut Microbiota With Special Emphasis on Host Nutrition", Curr. Protein. Pept. Sci., 2020.
Higashi, K. et al., "Hollow HydrogelMicrofiber Encapsulating Microorganisms forMass-Cultivation in Open Systems", Micromachines, 2017. 8(6): p. 176.
Wang, L. et al., "Dual-Functional Dextran-PEG Hydrohel as an Antimicrobial Biomedical Materials", Macromol. Biosci., 2018. 18(2).
Bunnak, J. et al., "Study on antibacterial activity of hydrogel from irradicated silk protein", 2001: Japan. p. 117-129.
Wichterie, O. et al., "Hydrophilic Gels for Biological Use", Nature, 1960. 185(4706): p. 117-118.

* cited by examiner

DEVICE FOR DETECTING A MEDICAL CONDITION OF A SUBJECT AND METHOD FOR MANUFACTURING THEREOF

TECHNICAL FIELD

The invention relates to a device for use in the field of medical detection and diagnosis, and particularly, but not exclusively, to a device for use with sanitary products for collecting and/or testing menstrual blood.

BACKGROUND ART

Menstrual blood possesses a great value for diagnosis of women's diseases. It contains endometrial tissues, cells from the mucus lining of the vagina, bacteria making up the vaginal flora, and biomolecules of the vaginal and uterus infection causing microbes. Research showed that HPV DNA was detected in menstrual blood from patient with cervical intraepithelial neoplasia (CIN) or condyloma acuminatum (CAC). Biomolecules from the menstrual blood possess the potential value for evaluation of fertility and detection of sexually transmitted diseases, infections and cancers. However, the collection of menstrual blood and the preservation of the biomolecules inside the menstrual blood are known to be difficult, hindering the use of menstrual blood for medical analysis.

Currently, collection of menstrual blood can be done by using a menstrual cup which is a cup-shaped device insertable into the vagina of a woman subject during menstruation. After the sample blood is collected in the cup, the subject will have to return the menstrual cup with the collected blood for immediate testing to thereby avoid denaturing or contamination of the blood. There are two problems associated with this collection method. First, the presence of the subject at the clinic or the testing laboratory is required for the immediate collection and testing of the menstrual blood. Menstruation period is not strictly regular and therefore, it is not always convenient for the subject to plan for a sample collection. Secondly, menstrual cups are still not commonly used by the majority of women due to, for example, discomfort or inconvenience during use, as well as cultural and hygienic issues associated with the use of the menstrual cup.

As an alternative, it is possible for the subject to send a used sanitary pad soaked with the subject's menstrual blood to the clinic or the testing laboratory for testing. However, it is understandable that the menstrual blood will become dried during the transportation and/or other handling processes, which will adversely affect stability of the biomolecules present in the blood sample. It is known that dehydration of biomolecules such as proteins results in significant, measurable conformational changes and may irreversibly inactivate some proteins and enzymes, for example, phosphofructokinase and lactatedehydrogenase. Addition of certain carbohydrates, e.g. disaccharides, may preserve the protein activity during either freeze-drying and/or air-drying by binding to the protein and thus, serving as a water substitute, when the hydration shell of the protein is removed. When the menstrual blood is collected by absorption at the sanitary pad, the blood will dry out completely within several hours, and that most biomolecules in the blood will no longer be stable at ambient temperature. Indeed, wet and dried biological samples revealed different biomolecules spectrum. For example, only wet virginal samples enable detection of low level (<100 copies) HPV. Dried sampling limits the types of biomolecules could be used for diagnostic biomarkers, hence posing a limited scope of diseases which could be detected using menstrual blood.

Moreover, microbes may have developed and overgrown when the sample arrived at the laboratory, which affect the accuracy of the downstream tests. A healthy vagina contains a balanced of yeast and bacteria flora. Bacteria, for example, *Staphylococcus aureus, Escherichia coli, Klebsiella-enterobacter* and Lactobacilli could be found in menstrual blood collected by a tampon, a cotton or a sponge. Yeasts, e.g. *Candida albican, C. glabrata, C. tropicalis* and *C. parapsilosi* are normally found in the vagina and thus, are expected to be found in the menstrual blood. Bacteria and yeasts use protein for their metabolism activities and will release enzymes for proteolysis. A used sanitary pad soaked with menstrual blood will usually develop a bad odor after a few hours to one day usage, depending on the ambient condition. The odor implies the growth of bacteria and yeasts and the subsequent degradation of organic matters in the sanitary pad. Menstrual blood is rich in nutrients and water content, providing an ideal condition for the growth of the bacteria and yeasts. With the presence of bacteria and yeasts, the protein content in the blood sample could be degraded or deactivated within a very short timeframe, resulting in a loss of value as a medical sample for diagnosis.

SUMMARY OF INVENTION

Technical Problem

An object of the present invention is to provide a device for detecting a medical condition of a subject from a body fluid which may include, but is not limited to, a menstrual blood collected from the subject.

Another object of the present invention is to provide a novel absorbent product such as, but is not limited to, a sanitary pad or napkin for detecting a medical condition of a subject from a body fluid, such as a menstrual blood, collected by the absorbent product.

A further object of the present invention is to provide device for collecting a body fluid from a subject of which constituent biomolecules of the body fluid can be collected, stabilized and/or preserved at suitable conditions for diagnosis.

A yet further object of the present invention is to mitigate or obviate to some degree one or more problems associated with known menstruation management and/or menstrual blood detection techniques, or at least to provide a useful alternative.

The above objects are met by the combination of features of the main claims; the sub-claims disclose further advantageous embodiments of the invention.

One skilled in the art will derive from the following description other objects of the invention. Therefore, the foregoing statements of object are not exhaustive and serve merely to illustrate some of the many objects of the present invention.

Solution to Problem

Technical Solution

In a first main aspect, the invention provides a device for detecting or diagnosing a medical condition of a subject from a body fluid collected from said subject. The device comprises a sampling member comprising one or more polymeric materials; the sampling member, when arranged to be in contact with the body fluid, collects constituent biomolecules of the body fluid at the polymeric materials; and a positioning member comprising an absorbing material, the positioning member being configured to support the sampling member; wherein the positioning member is releasably attachable to and is detachable from a substrate wearable by the subject.

In a second main aspect, the invention provides an absorbent product for detecting a medical condition of a subject from a body fluid collected from said subject. The absorbent product comprises an absorbing layer, a bottom layer arranged below the absorbing layer, and the device according to the first main aspect arranged at the absorbing layer.

In a third main aspect, the invention provides a sanitary product for detecting a medical condition of a subject from a body fluid collected from said subject. The sanitary product comprises a sampling member comprising one or more polymeric materials; the sampling member, when arranged to be in contact with the body fluid, collects constituent biomolecules of the body fluid at the polymeric materials; and a positioning member comprising an absorbing material, the positioning member being configured to support the sampling member; wherein the sampling member is removable from the positioning member after the constituent biomolecules are collected.

In a fourth main aspect, the invention provides a method of manufacturing the device according to the first main aspect. The method comprises the steps of providing a sampling member comprising one or more polymeric materials; the sampling member, when arranged to be in contact with a body fluid of a subject, collects constituent biomolecules of the body fluid at the polymeric materials; and providing a positioning member comprising an absorbing material, the positioning member being configured to support the sampling member; wherein the positioning member is releasably attachable to and is detachable from a substrate wearable by the subject.

In a fifth main aspect, the invention provides a method of manufacturing an absorbent product. The method comprises the steps of providing an absorbing layer, and a bottom layer positioned below the absorbing layer; providing the device according to the first main aspect at the absorbing layer; and providing an attaching means at the bottom layer for releasably attaching and detaching the absorbent product to and from a clothing of a user.

The summary of the invention does not necessarily disclose all the features essential for defining the invention; the invention may reside in a sub-combination of the disclosed features.

Advantageous Effects of Invention

BRIEF DESCRIPTION OF DRAWINGS

Description of Drawings

Figure 1A:
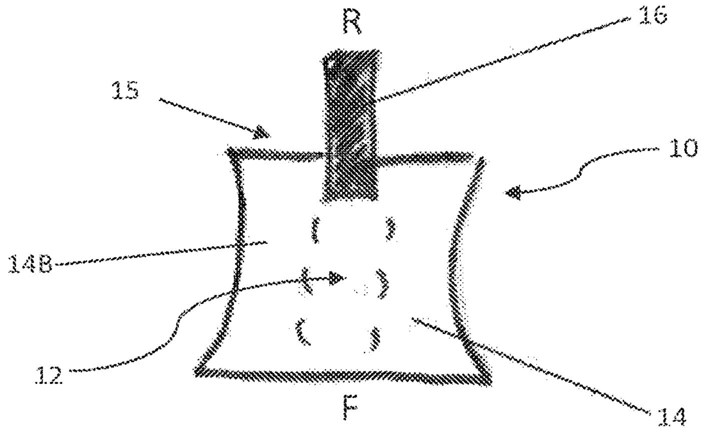
Figure 1B:
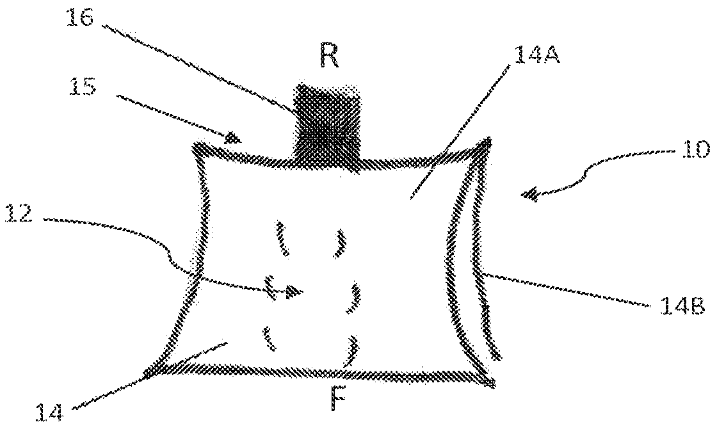
Figure 2A:
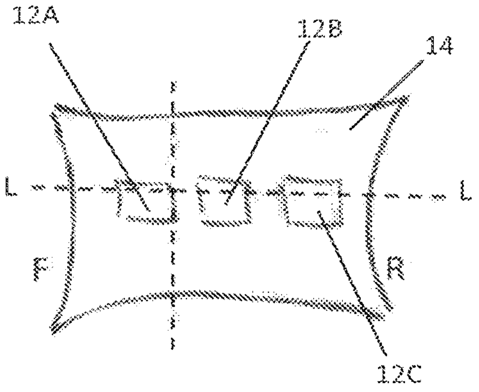
Figure 2B:
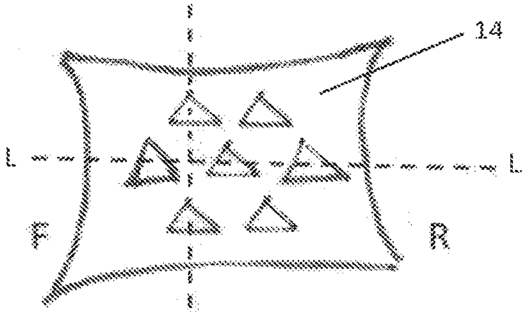
Figure 2C:
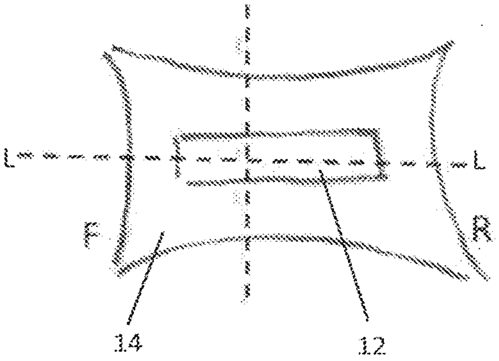
Figure 2D:
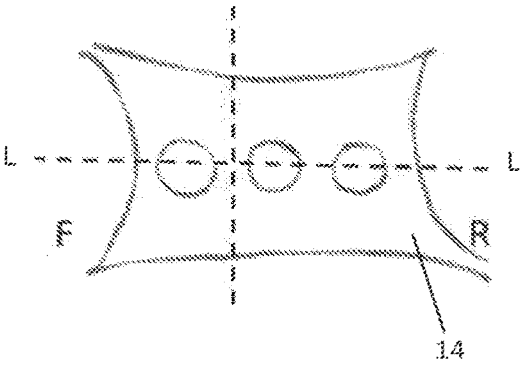
Figure 2E:
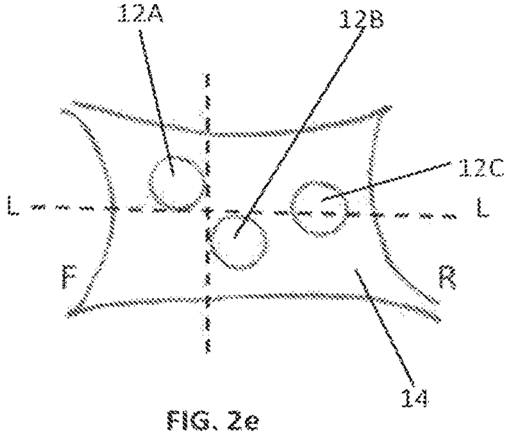

The foregoing and further features of the present invention will be apparent from the following description of preferred embodiments which are provided by way of example only in connection with the accompanying figure, of which:

FIGS. 1*a* and 1*b* are schematic diagrams showing the back side and the front side, respectively, of a device according to an embodiment of the present invention;

FIGS. 2*a*, 2*b*, 2*c*, 2*d* and 2*e* are schematic diagrams showing different embodiments of the sampling units of the device of FIGS. 1*a* and 1*b;*

Figure 3A:
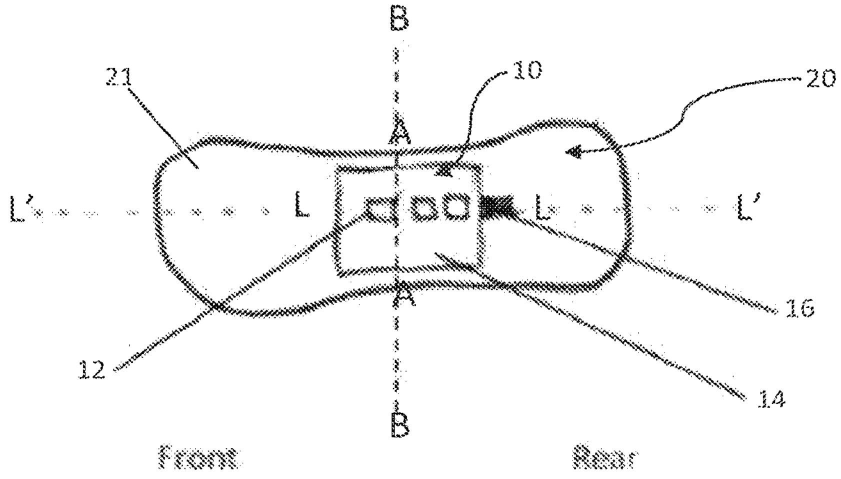
Figure 3B:
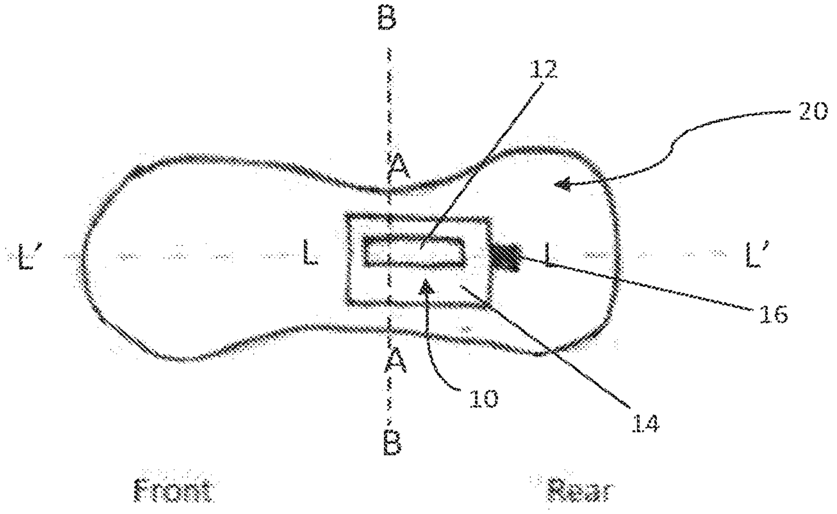
Figure 3C:
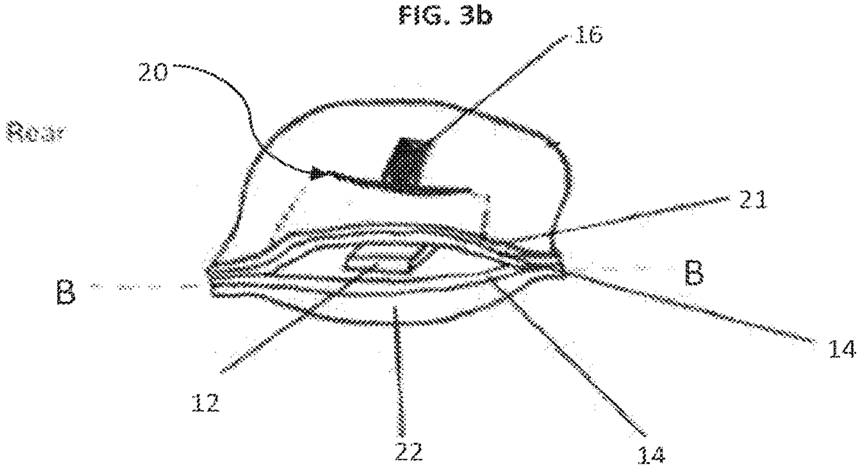

FIGS. 3*a* and 3*b* show the top view of a sanitary product according to an embodiment of the present invention with the device of FIGS. 1*a* and 1*b* arranged thereon; FIG. 3*c* is a cross-sectional view along a transverse axis of the sanitary product of FIG. 3*b;*

Figure 4A:
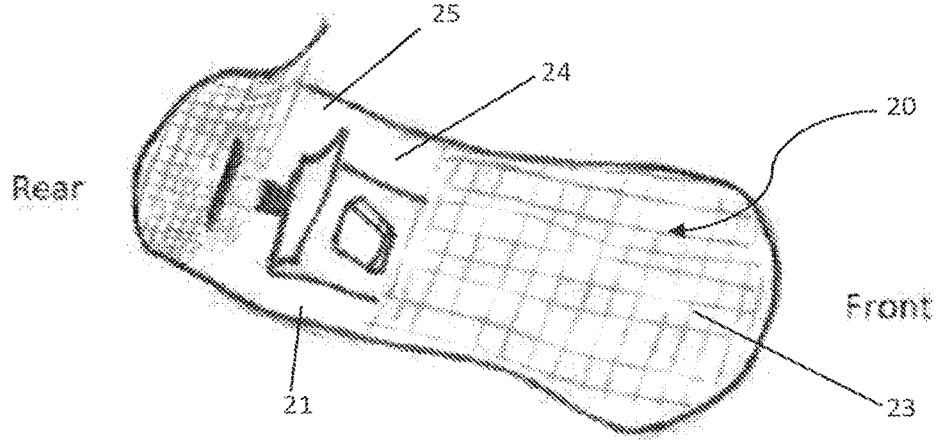
Figure 4B:
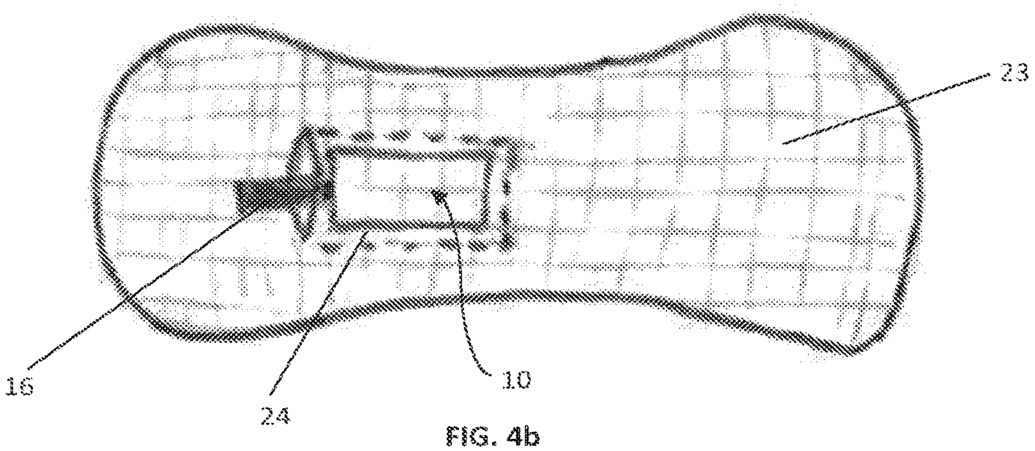
Figure 5A:
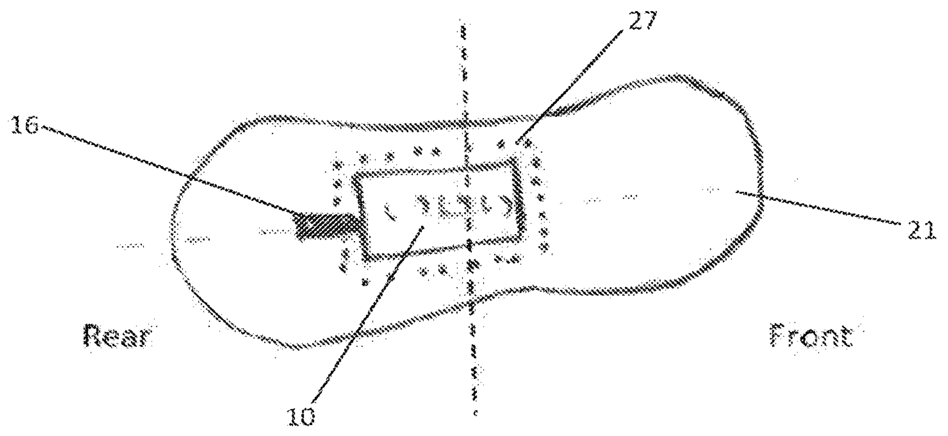
Figure 5B:
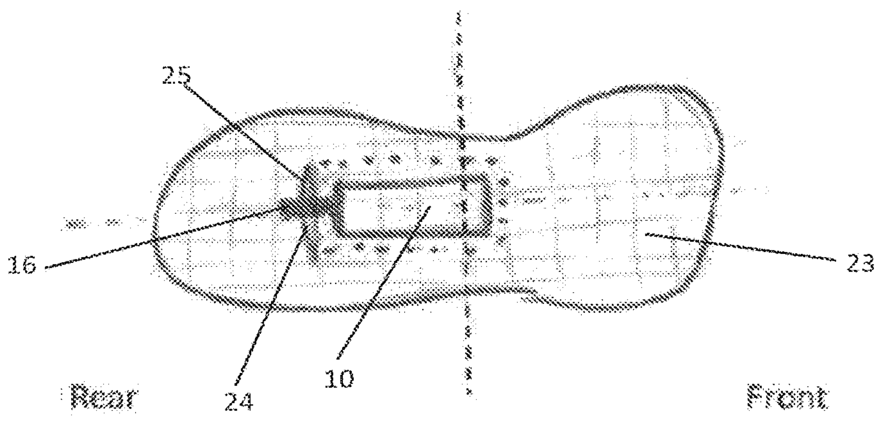
Figure 5C:
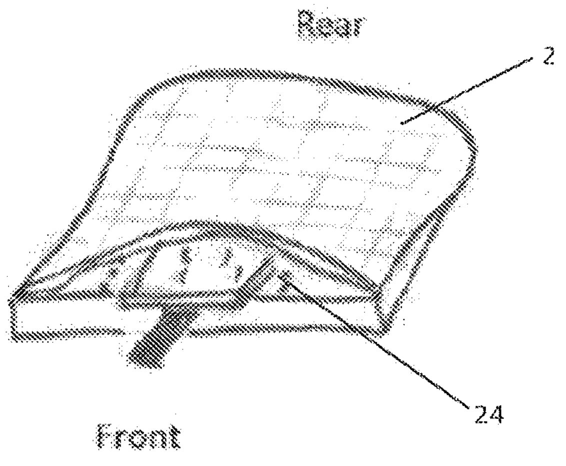

FIG. 4*a* is a schematic diagram of the sanitary product of FIG. 3*a* with a top layer of the sanitary product being opened to show the device therein; FIG. 4*b* is a schematic drawing of the sanitary product of FIG. 4*a* with the opening at the top layer closed;

FIG. 5*a* is a schematic diagram showing the sanitary product of FIG. 3*a* with the absorbing layer being configured with perforated lines for detachment of the device from the absorbing layer; FIG. 5*b* shows the sanitary product of FIG. 5*a* with a top layer provided above the absorbing layer; FIG. 5*c* is a cross-sectional diagram of the sanitary product of FIG. 5*b;*

Figure 6A:
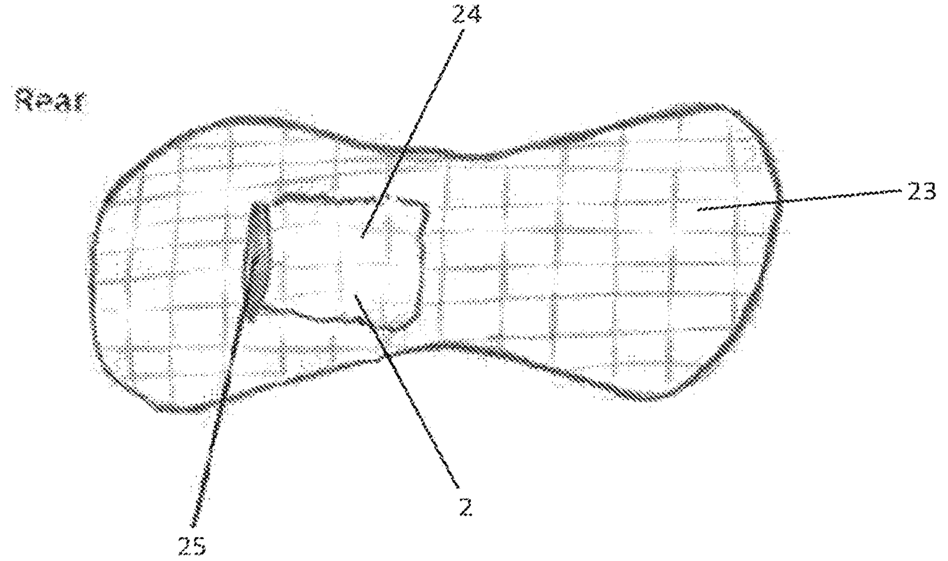
Figure 6B:
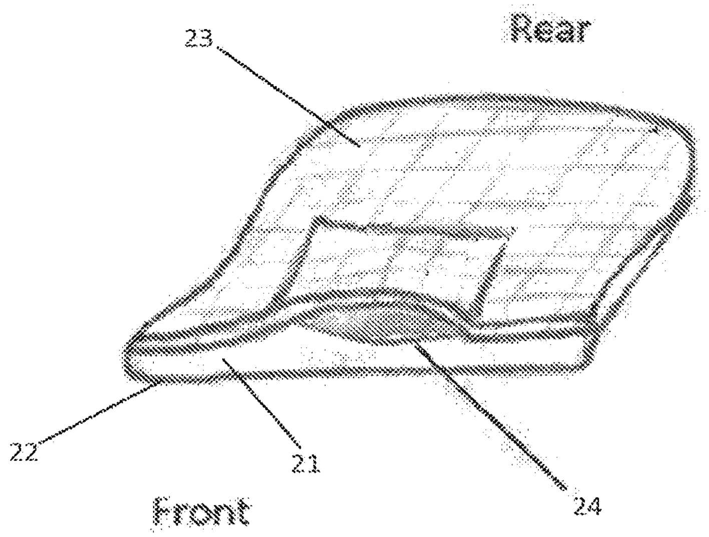

FIG. 6*a* shows a different embodiment of the sanitary product of the present invention, with the top layer and the absorbing layer being configured to define a pocket for accommodating the device; FIG. 6*b* shows a cross-sectional view of the sanitary product of FIG. 6*a;*

Figure 7:
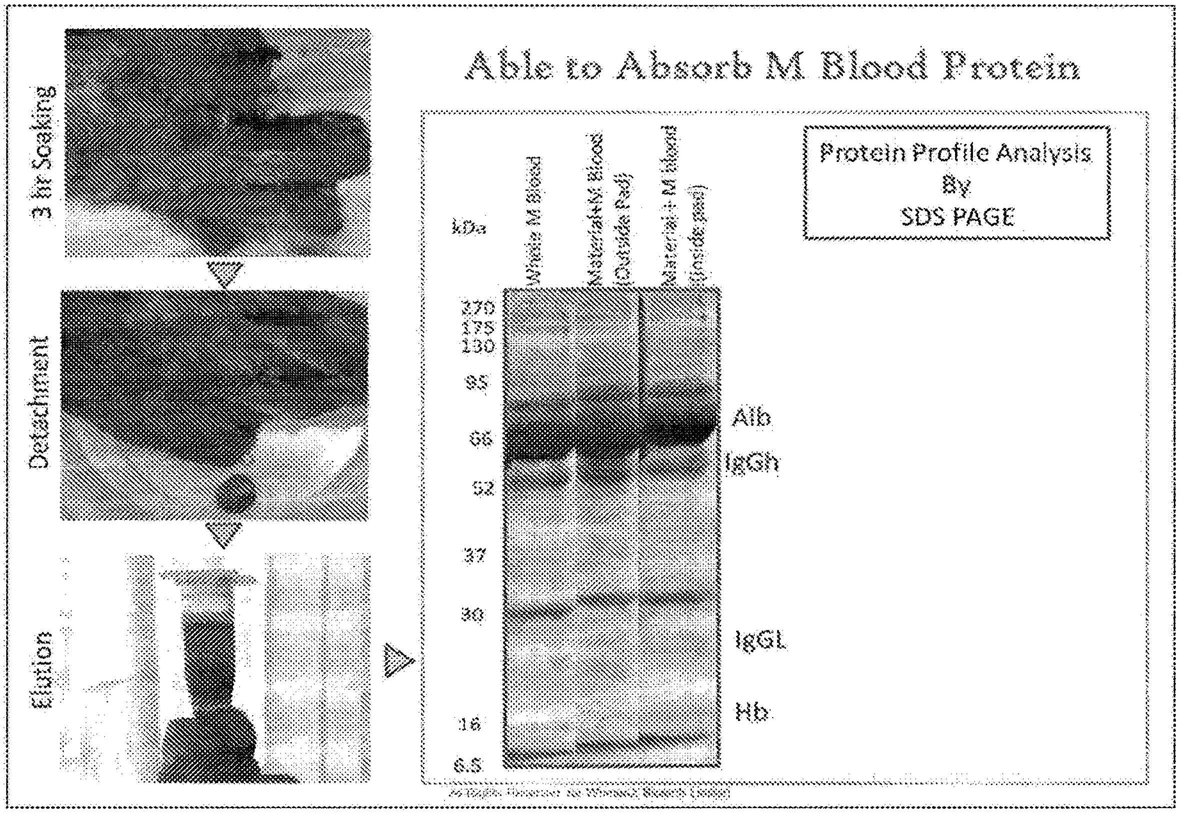

FIG. 7 illustrates the adsorption of protein by the hydrogel of the device of FIGS. 1*a* and 1*b;*

Figure 8:
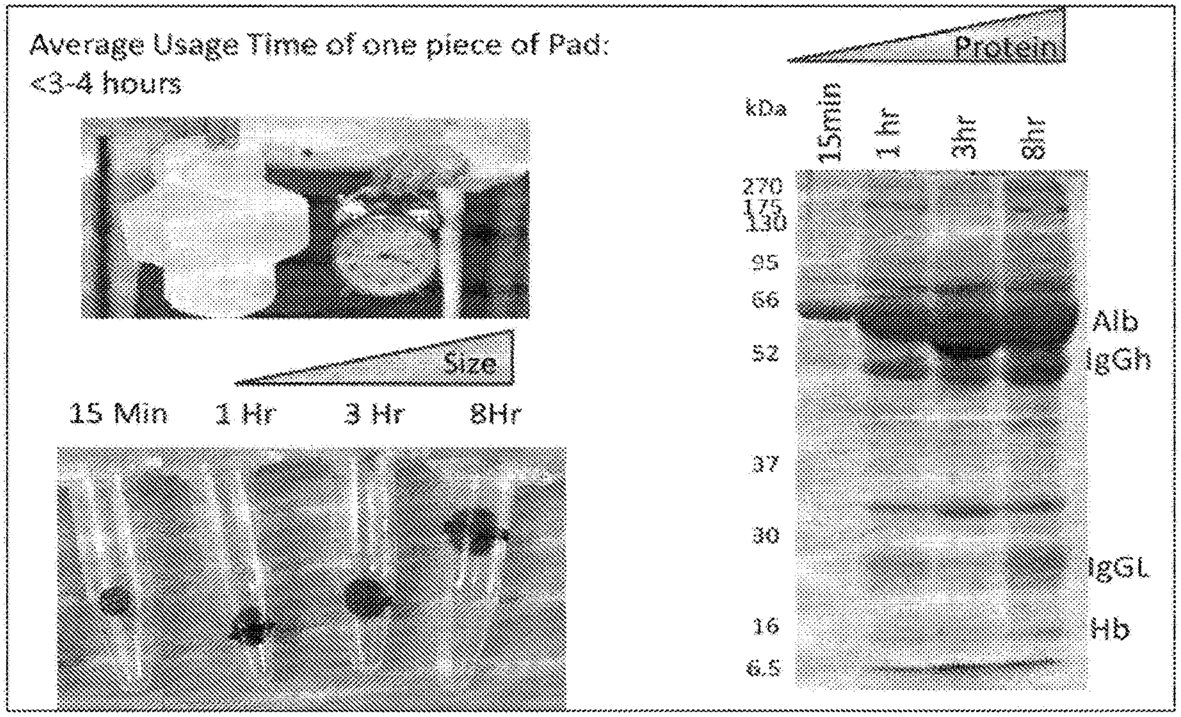
Figure 9A:
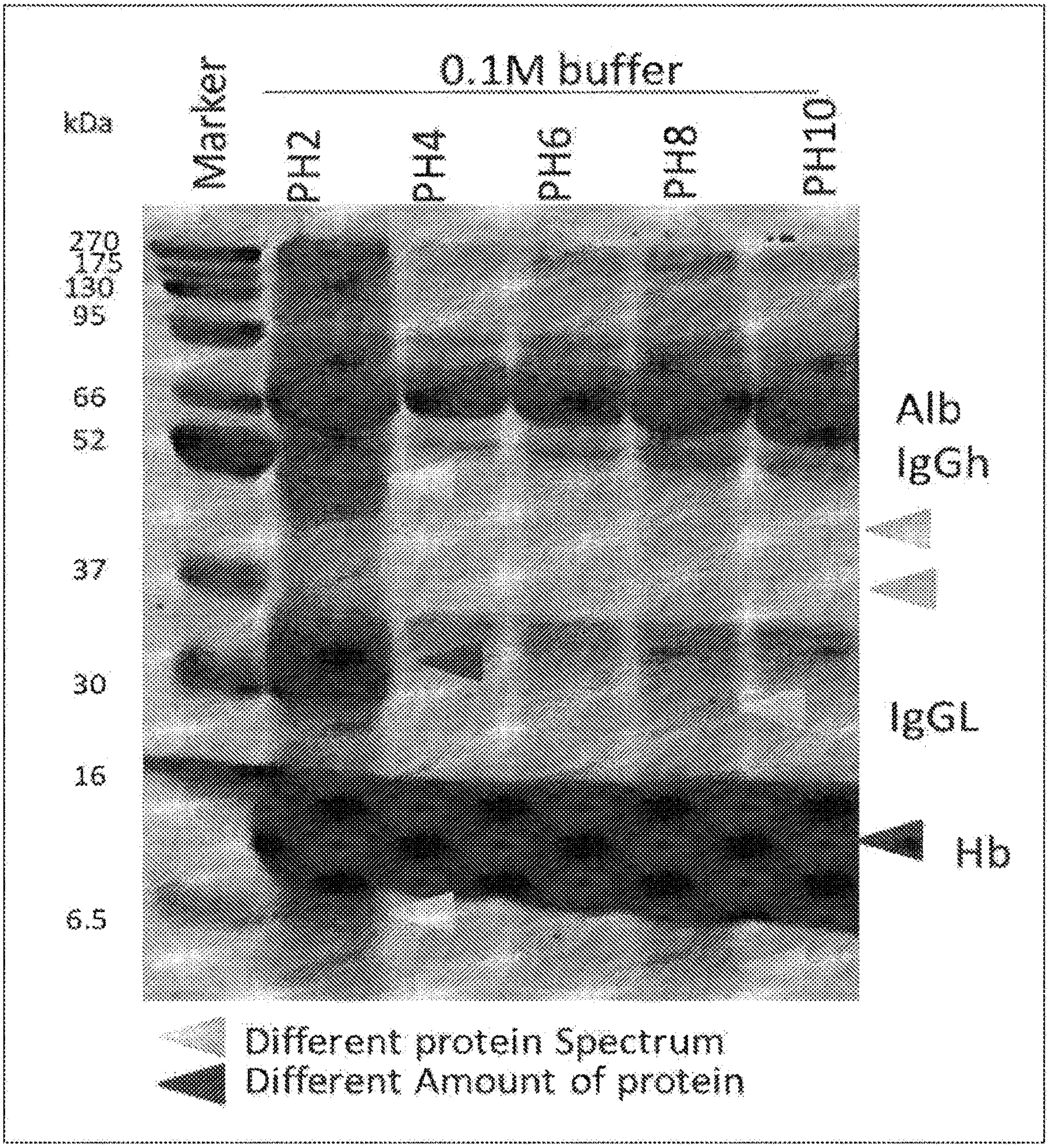
Figure 9B:
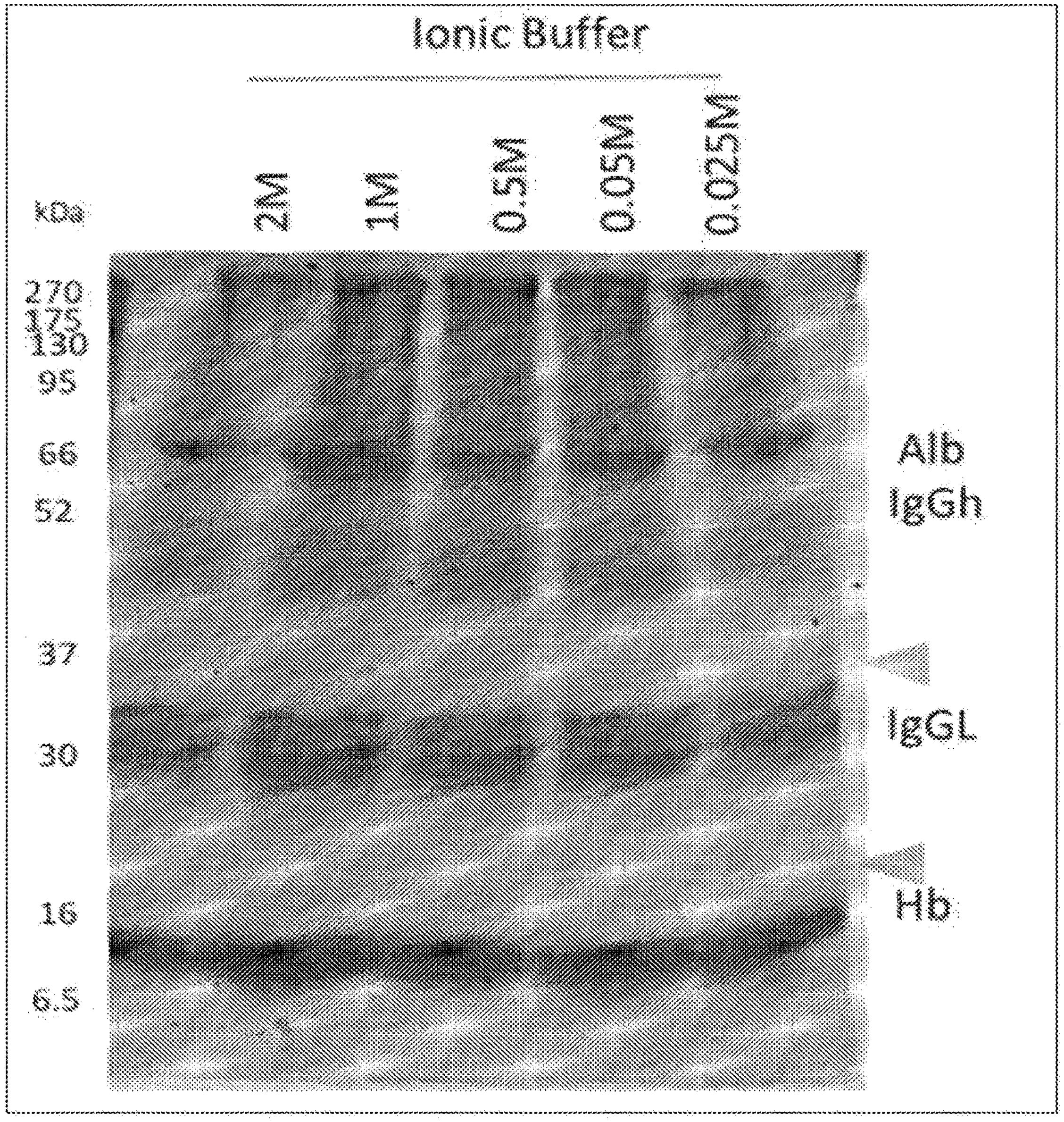
Figure 10:
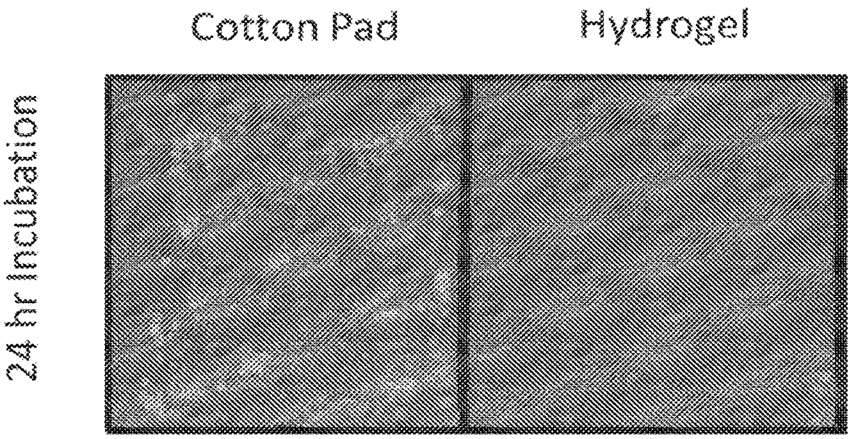
Figure 12:
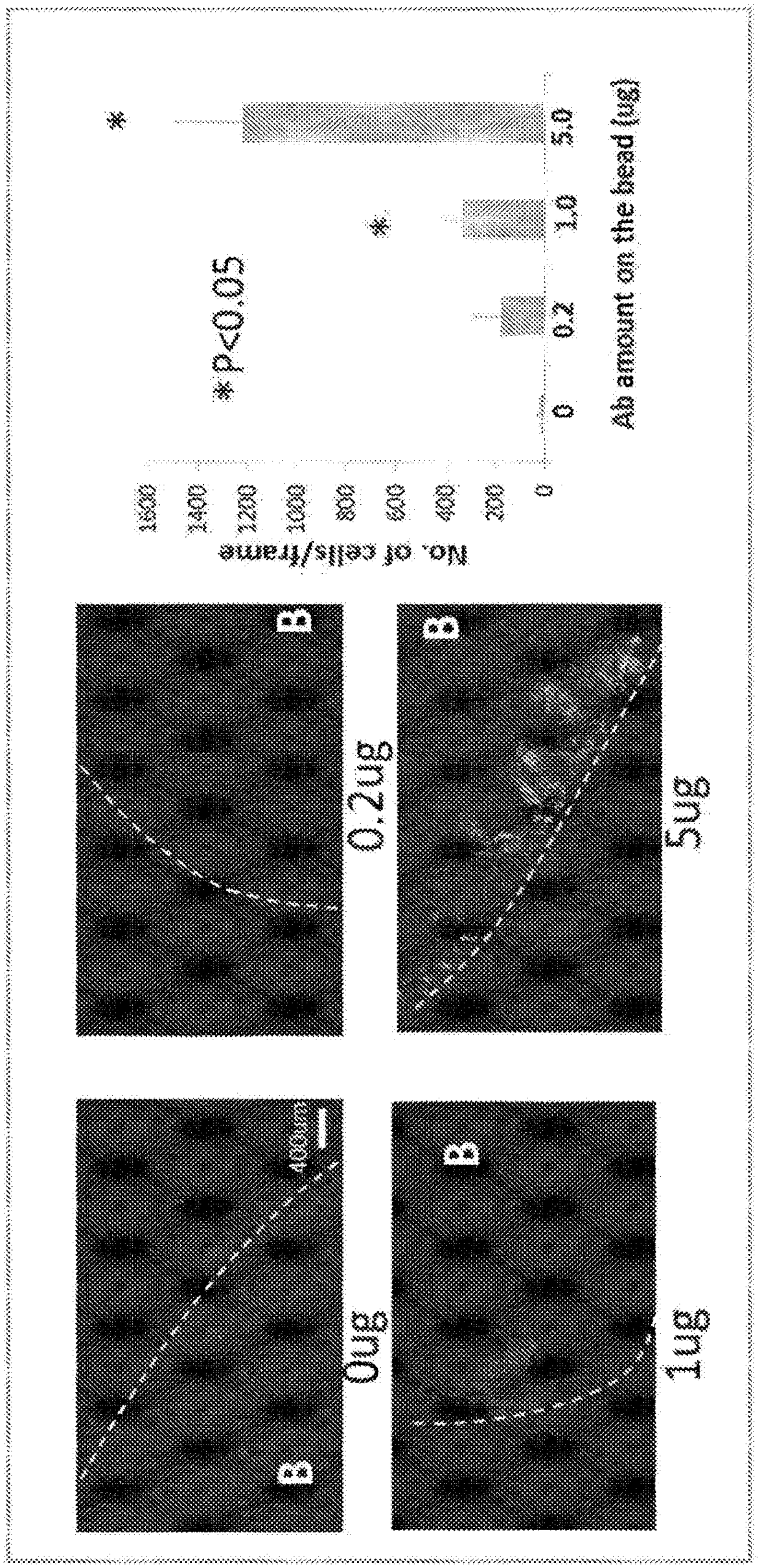
Figure 13:
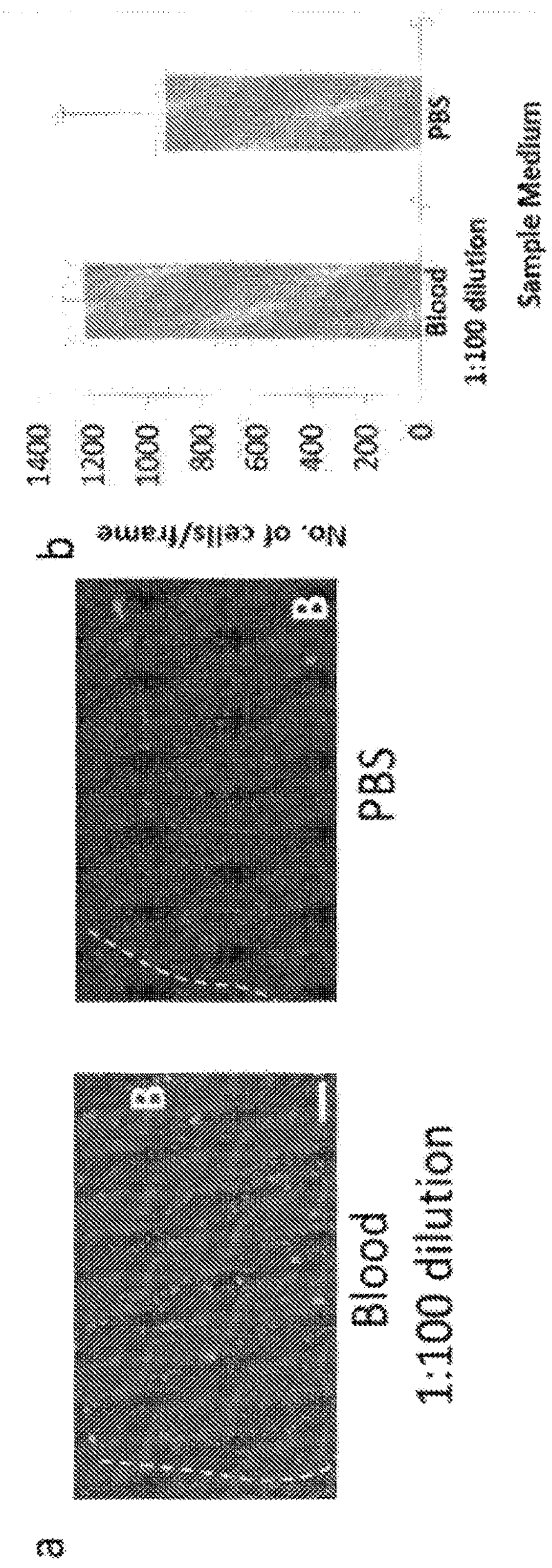
Figure 14:
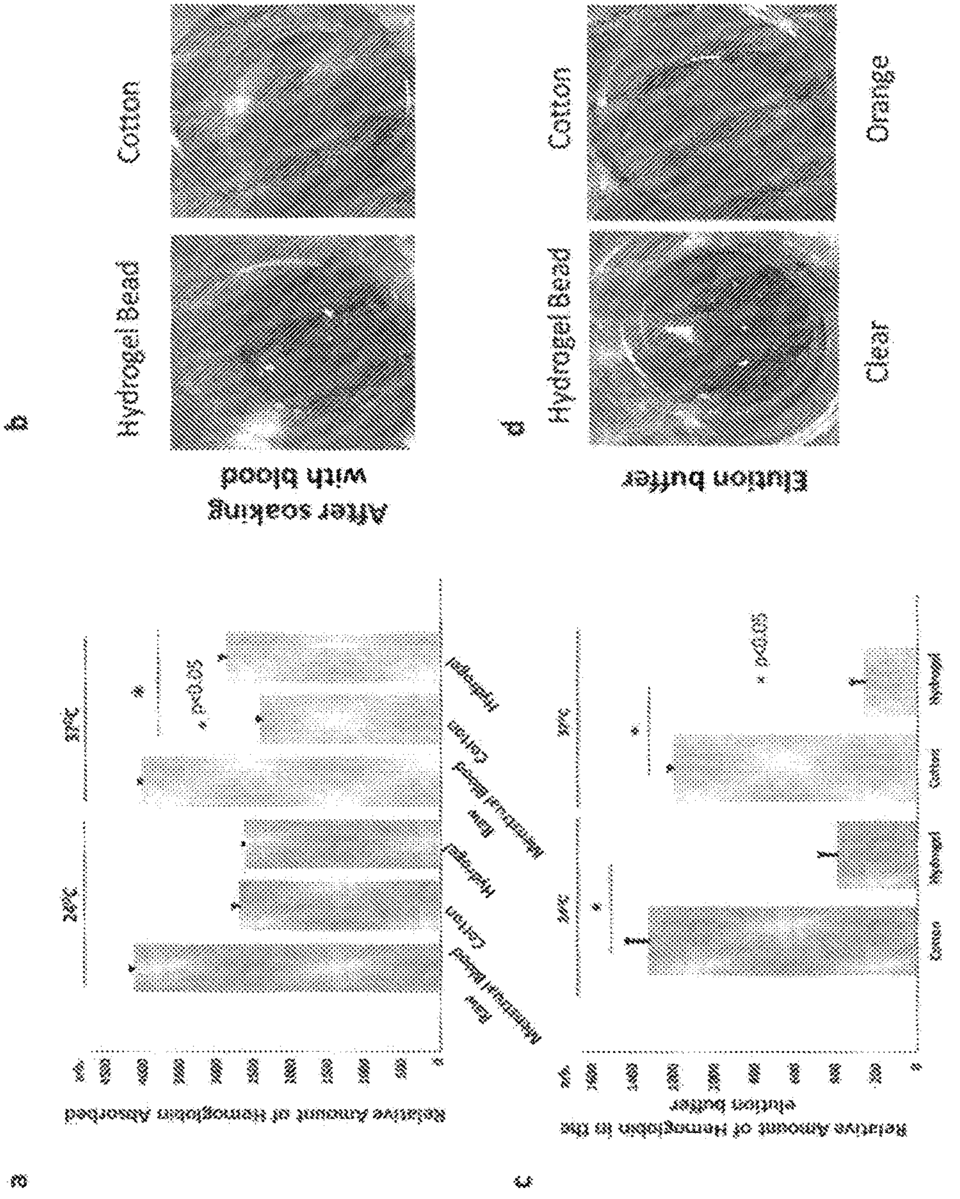
Figure 15:
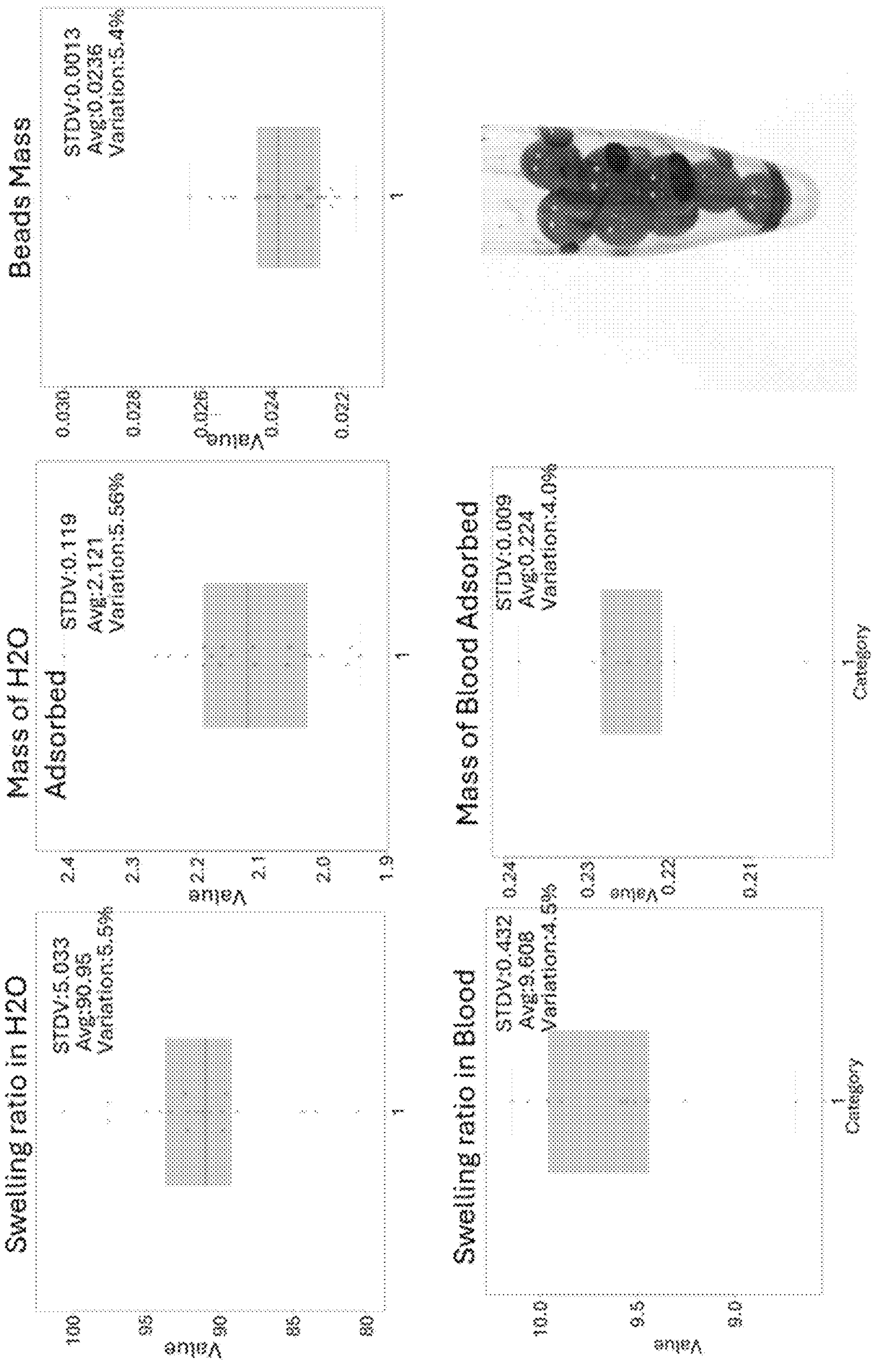

FIG. 8 illustrates the increase of protein adsorption with incubation time by the hydrogel;

FIG. 9*a* illustrates the selection of protein from the hydrogel by changing pH of the elution buffer; FIG. 9*b* illustrates the selection of protein from the hydrogel by changing ionic strength of the elution buffer;

FIG. 10 illustrates that the hydrogel has an inhibition effect to the growth of bacteria from the menstrual blood sample;

FIG. 11*a* illustrates the capturing of the cancer cells with target protein expressed by antibody conjugated hydrogel; FIG. 11*b* illustrates the capturing of the cancer cells with the conjugated hydrogel prepared with blocking protein; FIG. 11*c* illustrates the capturing of cells with lower target protein expression vs. the cancer cells with higher target protein expression;

FIG. 12 illustrates the effect of antibody dosage on the cancer cells with target protein expressed binding;

FIG. 13 illustrates the effect of blood content the cancer cells with target protein expressed binding;

FIGS. 14*a*, 14*b*, 14*c* and 14*d* show the hemoglobin absorption and elusion by hydrogel and cotton at the temperature 37° C. and 24° C.; and FIG. 15 shows the study on swelling ratios and mass on the hydrogel particles with water and blood.

MODE FOR THE INVENTION

Mode for Invention

The following description is of preferred embodiments by way of example only and without limitation to the combination of features necessary for carrying the invention into effect.

Reference in this specification to "one embodiment" or "an embodiment" means that a particular feature, structure, or characteristic described in connection with the embodiment is included in at least one embodiment of the invention. The appearances of the phrase "in one embodiment" in various places in the specification are not necessarily all referring to the same embodiment, nor are separate or alternative embodiments mutually exclusive of other embodiments. Moreover, various features are described which may be exhibited by some embodiments and not by others. Similarly, various requirements are described which may be requirements for some embodiments but not other embodiments.

The present invention relates to a device for use in detecting or diagnosing a medical condition of a subject based on a body fluid collected from said subject. Particularly, the present invention relates to a device which can be provided at or with an absorbent product such as, but is not limited to, a personal hygiene product such as a sanitary pad or napkin, and is releasably removable or detachable from the absorbent product after use, for example, after collection of a sufficient amount of menstrual blood as a sample for testing of health conditions or diagnosis for diseases.

In the context of the present invention, the term "body fluid" may generally relate to any fluids produced or secreted by, or discharged from a subject. The body fluids may include, but are not limited to, urine, blood including menstrual blood, vaginal discharge or secretion, post-surgery fluids, postpartum fluids, sweat, saliva, amniotic fluid, ascites and semen, etc. The term "absorbent product" herein referred to by the present invention may generally relate to any structures capable of absorbing a fluid. Examples of absorbent products may include, but are not limited to, sanitary pads, sanitary napkins, tampons, sanitary pants, panty liner, diapers such as baby diapers, adult diapers, postpartum diapers, post-surgical diapers, incontinence pad, and any general sanitary or personal hygiene products for fluid absorption, either disposable or reusable. The subjects can be human or animals. The term "medical condition" may generally cover any physiological and/or biological conditions, health conditions, illnesses and diseases or the like.

Referring to FIG. 1, shown is an embodiment of the device 10 according to the present invention. The device 10 may comprise a sampling member 12 comprising one or more polymeric materials, which can be synthetic or natural polymeric materials. The polymeric materials may comprise, but are not limited to, crosslinked polymeric materials. Preferably, the polymeric materials comprise one or more hydrogel materials.

In one embodiment, the hydrogel materials may comprise synthetic materials such as, but are not limited to, one or more of polyacrylic acid, poly(ethylene oxide), poly(2-hydroxyethyl methacrylate), 2-Hydroxyethyl methacrylate, polyglycidol, polysaccharides, poly(N-isopropylacrylamide), polyacrylate, polypropylene, polyester, polyethylene, polyurethane, polyvinyl alcohol, polyethylene glycol, polyacrylamide/acrylic acid copolymer, ethylene maleic anhydride copolymer, cross-linked carboxymethyl-cellulose, polyvinyl alcohol copolymer, cross-linked polyethylene oxide, sodium polyacrylate, microporous cellulose, carbohydrate acrylic copolymer, and starch grafted copolymer.

The hydrogel materials may be synthesized any known polymerization techniques such as but are not limited to one or more of the inverse suspension polymerization, the free-radical polymerization and/or the reversible addition-fragmentation chain-transfer (RAFT) polymerization. In one specific embodiment, cross-linked polyacrylate acid (PAA) polymer with molecular weight of about 45 kDa to about 100 kDa is prepared in spherical shape. For example, the crosslinked PAA polymer can be synthesized via free-radical polymerization as follows:

Acrylic acid monomers are neutralized with sodium hydroxide solution. Potassium persulfate is the initiator while polyethylene glycol dimethacrylate is the crosslinker. Ethyl cellulose is the surfactant and cyclohexane is used as the solvent for the nonaqueous phase. The initiator and the crosslinker are added to the aqueous phase containing the sodium acrylate. Nitrogen gas is then blown into the aqueous and nonaqueous phases to remove the oxygen. The aqueous phase containing the monomers, initiator and the crosslinker is then transferred to the non-aqueous phase in a dropwise manner. The polymerization will be carried out for a predetermined period and after the polymerization is completed, cyclohexane is removed by distillation under reduced pressure. The synthesized hydrogel beads or particles were then collected by drying under high temperature.

The molecular weight and concentration of the synthesized polymer will affect the pore size of the formed crosslinked hydrogel and the compression force of hydrogel product.

In one embodiment, the hydrogel materials may comprise natural materials such as, but are not limited to, one or more of collagen, fibrin, hyaluronic acid, matrigel, chitosan, cotton, cellulose, alginate and silk fiber.

In one embodiment, the hydrogel materials forming of the sampling member 12 may comprise a three-dimensional (3D) network formed by chemical or physical crosslinking of individual polymer chains which physically trapping and engaging the biomolecules and preserving their structure. In one embodiment, the hydrogel materials may engage or bind the biomolecules via diffusion, hydrophobic interaction, and/or electrostatic attraction. The high water content of the hydrogel further stabilized the biomolecules by preventing the biomolecules from dehydration. The hydrogel materials can be negatively charged, positively charged or with no net charge, and preferably, negatively charged. The hydrogel material can also be hydrophilic or hydrophobic, and preferably, hydrophilic in nature. For example, the negative charges and/or the hydrophilicity of a hydrogel material prevent binding of negatively charged, hydrophilic microbes, with most of the microbes presented in the menstrual blood are negatively charged and are hydrophilic in nature.

Preferably, the hydrogel materials are provided in the form of particles. In one embodiment, the hydrogel particles are provided in particle sizes i.e. with diameters ranging from about 0.5 mm to about 5 mm, and more preferably, about 1 mm to about 3 mm. Preferably, the hydrogel can be porous, with pore sizes ranging from nano to micro scale, and more preferably, about 1 μm to about 20 μm. The small pore sizes is found to limit the space available for the microbes to grow and multiply, and therefore, inhibit the growth and multiplication of the microbes.

Prior to usage of the device by a subject, it is preferred that the hydrogel materials at the sampling member 12 be kept in a dried condition. The hydrogel sampling member 12, when arranged to be in contact with the body fluid, such as the menstrual blood of the subject, will absorb the blood and expand in volume. The expanded hydrogel collects and preserves the constituent biomolecules of the menstrual blood. In the context of the present invention, the term "constituent biomolecules" relates generally to biomolecules which form a component part of the body fluid, which may include, but are not limited to, cells such as blood cells, nucleic acids such as RNA, DNA, miRNA, proteins, antigens, antibodies, enzymes, etc. Without limiting by any specific embodiments, a person skilled in the art will appreciate that the biomolecules as referred to in the present description may include any analytes present in a body fluid.

The device 10 may further comprise a positioning member 14 configured to support the hydrogel-based sampling member 12. Preferably, the positioning member 14 comprises an absorbing material, such as cotton, rayon, polyester, non-woven gauze, silk, and/or any other materials having absorption rates comparable to that of cotton. In one embodiment, the positioning member 14 is configured to be releasably attachable to, and is detachable from a substrate wearable by the subject. In the context of the present description, the term "substrate" may refer to an absorbent product such as, but are not limited to, a personal hygiene product or a medical product such as a sanitary pad or napkin, sanitary pants and/or any absorbing materials adapted to support or carry the device 10 for the purpose of collecting the body fluid such as the menstrual blood. In one specific embodiment, the positioning member 14 is preferred to be in a rectangular shape, such as in a dimension of about 4 cm×about 5 cm (length×width) and more preferably, not less than about 2 cm×about 1 cm (length×width), with a preferable thickness from about 2 mm to about 6 mm. Without limiting by any examples, a person skilled in the art will appreciate that the size of the sampling member 12 and/or the positioning member 14 would be variable depending on the size of the supporting substrate such as the sanitary pad carrying the device 10.

In one embodiment, the positioning member 14 may comprise at least two absorbing layers, such as an upper layer 14A and a bottom layer 14B, with the sampling member 12 being arranged therebetween. Preferably, the bi-layers structure of the positioning member 14 can be configured in the form of a pocket, with at least one opening 15 for receiving and removing the hydrogel-based sampling member 12. The pocket-like configuration of the positioning member 14 allows the sampling member 12 be positioned and be kept in place by friction, for example, between the two absorbing layers 14A, 14B.

FIG. 2 further illustrates the arrangement of the hydrogel sampling member 12 at or within the positioning member 14. As shown in the figure, the sampling member 12 comprises one or more hydrogel sampling units 12A, 12B, 12C, for example, planarly arranged, i.e. without overlapping, between the at least two layers of the positioning member 14. At least one of the sampling units can be arranged to align along a longitudinal axis L-L of the device 10 (see FIGS. 2*a*, 2*b*, 2*c* and 2*d*, for example), or can be disposed randomly but planarly within the pocket of the positioning member 14 (see FIG. 2*e*). The sampling member 12 is not restricted to comprise any number of sampling units, which may vary from one to up to tens or hundreds of very small sized sampling units, depending on the specific requirements and applications of the device 10. The sampling units 12A, 12B, 12C can be configured in any 2-dimensional shapes which may comprise one or more shapes of a square, a rectangle, a triangle, a circle, a strap, a polygon, and an irregular shape, etc.; or in any 3-dimensional shapes, which may comprise one or more of a cuboid, a sphere, a pyramid, a prism, a cylinder, and a polyhedron, etc. In one specific embodiment, a sampling unit of a shape of a square may preferably of a dimension of about 0.5 cm×about 0.5 cm×about 1 cm (length×width×thickness) in it maximum expanded state in blood (see FIG. 2*a*). If the sampling unit is of a rectangular shape (see FIG. 2*c*), the dimension may preferably be about 0.5 cm×about 2 cm×about 1 cm (length×width×thickness) in its maximum expanded state in blood. If the sampling unit is of a circular shape (see FIGS. 2*d* and 2*e*), the diameter may preferably be of about 1 cm with a thickness of about 1 cm in its maximum expanded state in blood. If the sampling unit is in a triangular shape, the base and the height of the triangular unit may preferably be of about 1 cm×about 1 cm with a thickness of about 1 cm in its maximum expanded status in blood. The sampling units may further be porous or may comprise microchannels to increase the surface area to volume ratio of the hydrogel sampling units for a more efficient capturing of the biomolecules.

Preferably, the device 10 may further comprise a detaching means 16 for detaching the device from the substrate wearable by the subject. The detaching means 16 can be provided in the form of a tag, a peel or a string, which generally take the form of or comprises an elongated structure extending away from the positioning member 14 to allow an easy gripping and pulling by the user when it is desired to remove or detach the device 10 from the substrate such as a sanitary pad. In one embodiment, the detaching means 16 is attached to a bottom layer 14B of the positioning member 14 by means of, for example, heat sealing, compressed sealing, gluing or adhesive or sewing. The peel 10 is preferably formed of material which is not soluble and is not easily deformable in wet condition, and more preferably, be prepared in a contrasting color from the absorbent product to thereby allow an easy identification of the peel 16 by the user. Preferably, the peel 16 is of a dimension of about 2 cm×about 1.5 cm (length×width), and more preferably, about 1 cm×about 0.5 cm (length×width), with a thickness of less than about 0.5 mm. The peel 16 is preferably positioned at a rear end (R) distal to the front end (F) of the device 10.

FIGS. 3*a* and 3*b* further illustrate arrangements of the device 10 at an absorbent product such as a sanitary pad 20. A typical sanitary pad 20 may generally comprise at least an absorbing layer 21 for absorbing menstrual blood, and a bottom, water-proof layer 22 under the absorbing layer 21 (as shown in FIG. 3*c*). A top layer 23 may optionally be provided above the absorbing layer 21, with the top layer 23 being the layer most adjacent to the user's skin in use, see for example, FIGS. 4*a*, 4*b*, 5*b*, 5*c*, 6*a* and 6*b*. The top layer 23 is generally included to improve skin feel of the user. As shown in the figures, the device 10 can be arranged on or at the absorbing layer 21. In one embodiment, the device 10 can be attached on the upper surface of the absorbing layer 21 by adhesive such as gluing or sealing including heat sealing or compressed sealing, etc. Alternatively, the device 10 may also be connected to the absorbing layer 21 by sewing at the layer 21, or for the positioning member 14 being integrally formed as part of the absorbing layer 21. In one preferred embodiment, for a sanitary pad 20 having a top layer 23, the top layer 23 and the absorbing layer 21 can be configured to define a cavity 24 for receiving the device 10. Preferably, the top layer 24 may comprise an opening 25 for receiving the device 10 into the cavity 24 (see FIGS. 4*a*, 5*b*, 6*a* and 6*b*). The cavity 24 can be formed by compress sealing or heat sealing one or more portions of the top layer 23 with the absorbing layer 21 (see FIGS. 5*b* and 5*c*), or the cavity 24 can be provided in the form of a pocket between the top and the absorbing layer 23, 21 (see FIGS. 6*a* and 6*b*). For example, when the sanitary pad has been worn for a defined period, such as no less than 3 hours, the user may open the top layer 23 from the opening 25 located at the rear end of the pad 20, grip the extended end of the peel 16, and then pull the device out from the cavity 24 via the opening 25 to thereby remove the device 10 from the sanitary pad 20. In yet another embodiment, at least part of the absorbing layer 21 is perforated 27 to facilitate an easy detaching of the device 10 from the absorbing layer 21.

Preferably, the device 10 is positioned at the absorbing layer 21 such that a longitudinal axis L-L of the device 10 is aligned with a longitudinal axis L'-L' of the absorbent product 20, see FIGS. 3*a* and 3*b*. The device 10 is positioned with a front end (F) of the device 10 facing a front end of the absorbent product 20, i.e. with a rear end (R) of the device 10 facing a rear end of the absorbent product 20. More particularly, it is preferred for the transverse axis A-A of the device 10, which is perpendicular to the longitudinal axis L-Land defining one-third (d) of a longitudinal length from the front end of the device 10, as being overlapped with a central transverse axis B-B of the absorbent product, with the central transverse axis B-B of the absorbent product 20 being perpendicular to the longitudinal axis L'-L' of, and defining half of a longitudinal length of the absorbent product 20, see FIGS. 3*a* and 3*b*.

An attaching means (not show) such as an adhesive may further be provided at, such as at a lower surface of, the bottom layer 22 for attaching the sanitary pad 20 to a surface of the clothing such as an under pant of the subject.

Passive Collection of Menstrual Blood

FIG. 7 showed, at the left column, a detached device 10 after the sanitary pad has been used for 3 hours. The hydrogel sampling member 12 was removed from the positioning member 14 for protein elution. Further showed at the right column of FIG. 7 are the results from the sodium dodecyl sulphate-polyacrylamide gel electrophoresis (SDS PAGE) showing profile of the protein eluted from the menstrual blood sample collected by the hydrogel sampling member. Control experiments conducted by testing raw menstrual blood (Whole M Blood) and by soaking the raw menstrual blood in a hydrogel (Outside Pad) under the same conditions showed similar profile. The results demonstrated that the device of the present invention is capable of collecting most of the protein in the menstrual blood. FIG. 8 further showed the protein amount collected by the hydrogel sampling member increases with time of usage of the carrying sanitary pad. The amount of protein collected is found to increase after 15 mins, 1 hour, and is levelled off, i.e. reaching a maximum absorption after three hours of usage, with no significant changes in the amount of protein collected after 8 hours of usage.

Water Retention to Maintain Stability of the Biomolecules Collected

As previously discussed, dehydration of biomolecules such as proteins may result in significant conformational changes and may completely and irreversibly inactive some proteins and enzymes in the blood sample. When the menstrual blood is collected by the sanitary pad, the blood will dry out completely within several hours and that most biomolecules present in the blood sample are not stable at ambient condition. The present invention is advantageous to allow stabilization of the collected biomolecules in the menstrual blood by using hydrogel as the sampling material. Hydrogel is a hydrophilic polymer which absorbs and retains water to prevent dehydration of the biomolecules due to water loss. It therefore stabilizes the biomolecules during use of the sanitary pad and/or during transportation of the device or the sampling member to the testing laboratory for the subsequent diagnosis. Structures of the biomolecules are maintained by the high water content of the hydrogel even after 48 hours after the menstrual blood sample is collected which enables an accurate and high sensitivity detection assay.

Selection of Specific Protein for Diagnosis

The hydrogel material is found to be sensitive to pH, electric field and temperature. By eluting the biomolecules from the hydrogel at specific conditions such as at a predetermined pH, charges, ionic strength and/or temperature, specific biomolecules such as proteins or cells can be selectively eluted and extracted from the sampling member. For example, polyacrylic acid hydrogel has a pKa of 4.5 and is negatively charged at a neutral pH 7. The variations in the pH, concentration of salt and temperature conditions affect the binding strength of the biomolecules on hydrogel. By changing the pH and the salt concentration of the elution buffer, for example, different proteins will be eluted and extracted from the hydrogel polymer.

FIGS. 9*a* and 9*b* showed the different elution profiles of proteins when the hydrogel material from a used device after menstrual blood collection was incubated in buffers with different pH and salt concentration, respectively. It was found that temperature may also affect the strength of binding and interaction between the biomolecules and the hydrogel material. Variation in temperature allows control of the amount or the type of proteins being eluted from the hydrogel, as protein has different binding strength towards the hydrogel in different temperature, e.g. a weaker binding is observed at a lower temperature. The results demonstrated that different specific biomolecules can be selected to be eluted from the used hydrogel material based on different elusion strategies to avoid or minimise elusion of any non-targeted biomolecules to thereby facilitate a more specific assay at the subsequent diagnostic procedure.

Modification and Coupling with Biosensors

Hydrogel can be modified chemically for conjugation with different bioreceptors which enable detection of various biomolecules, including but are not limited to proteins, DNAs, RNAs and cells. In one embodiment, the hydrogel materials of the device of the present invention can be coupled, attached or conjugated with one or more biosensing molecules specific to the targeted biomolecules. The biosensing molecules can be one or more of, for example, nucleic acids such as any forms of DNAs and/or RNAs, proteins, antigens or antibodies, enzymes, cells, cellular structures, biomimetic materials, functional particles, metals and small molecules. Antibodies allow identification of antigens, viruses, and bacteria. Enzymes allow quantifying of catalytic reactions. Aptamers such as oligonucleotides or peptide molecules allow capturing of nucleic acids. Cells or cellular structures are examples of chemical-specific biosensors which allow chemical sensing in the collected sample. Biomimetic receptors are artificial mimics of bioreceptors. On top of conjugation, application of fabrication patterning techniques including micromolding, microlithography e.g. photomask, ion beam, and optical maskless, etc., wet-etching, microcontact printing, and evaporation-induced self-assembly may also be applicable to the modification and coupling of the hydrogel materials of the present invention.

Anti-Microbial Effect of the Hydrogel Material

Growth of microbials such as bacteria, fungi and/or viruses will degrade, denature or deactivate the collected biomolecules. In order to preserve the proteins and/or other biomolecules from the collected menstruation blood making it suitable for medical diagnosis, the hydrogel materials of the device of present invention are found to demonstrate an inhibition effect to suppress bacterial, fungal and viral growth. Reasons for the hydrogel material's antimicrobial action may include (i) the hydrogel retains large amounts of water which causes membrane rupture of the bacteria, (ii) hydrogel does not contain organic matters to support growth of the bacteria and to maintain their survival, (iii) hydrogel contains net charges which inhibit the growth of the bacteria, and/or (iv) small pore sizes of the hydrogel materials which prevent entry of the microorganism. It is further discovered that the hydrogel material of the present invention prevents adhesion of the cells of the microbials in forming biofilms due to the hydrophilicity and electrostatic force of the hydrogel material, while the small pore sizes of the cross-linked structure further limit the subsequent growth of the microbials. Further studies supported that the negatively charged, hydrophilic nature of the hydrogel material is highly potent in suppressing the growth of microbes present in menstrual blood.

FIG. 10 showed the bacterial inhibitory effect of the hydrogel material of the present invention. In this experiment, 100 μl of menstrual blood was added to a 0.5 cm×0.5 cm of cotton of a sanitary pad, and a hydrogel material of the sampling member of the present invention separately. After 24 hours of incubation, 1000 μl of buffer solution was added to the samples. 5 μl of each sample was taken out and was spread on a TSA agar plate. The bacterial growth in the menstrual blood as collected by the hydrogel material was found to be much lower than the sample with menstrual blood being incubated in the cotton pad.

Capturing of Cancer Cells with Target Protein Expressed

Binding Ability and Specificity

Figure 11:
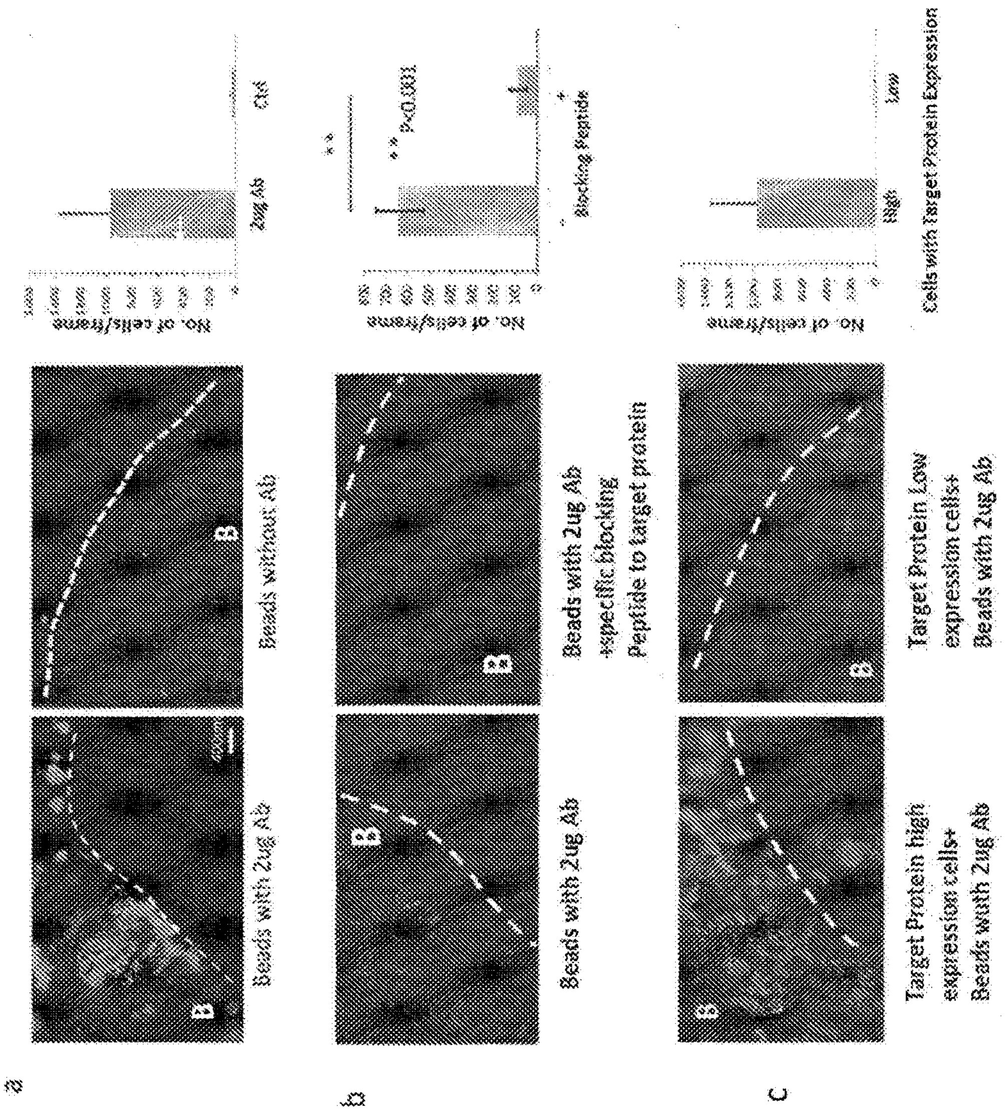

The ability of the antibody conjugated polyacrylic acid (PAA) hydrogel particles for capturing the cancer cells with target protein expressed was examined. The presence of cancer cells is an indicator of a disease. The PAA hydrogel particles conjugated with the antibody biosensor against the target protein was capable in capturing the cancer cells which expressed the target protein, indicating the presence of the cancer cells in a medium. The expression of the target protein distinguished the cancer cells from the normal cells. A cancer cell line which expressed abundant target protein was identified. The cancer cells with target protein expressed are then incubated with the polyacrylic acid (PAA) hydrogel particles conjugated with the respective antibody. A control experiment with PAA hydrogel particles with no conjugation is prepared separately. The results are shown in FIG. 11. Specifically, the dotted lines in the images outline the boundary of the hydrogel sample, with the presence of the hydrogel particles indicated by "B". The other side of the boundary does not contain any hydrogel particles. The white dots represent the cancer cells. The results demonstrated that the PAA hydrogel particles with antibody conjugation is found to capture 100 folds more cancer cells with target protein expressed than those without conjugation (see FIG. 11*a*).

Another sample of conjugated PAA hydrogel particles is further prepared with specific blocking peptide which blocks interaction between the cancer cells with target protein expressed and the antibody against the target protein. The binding of the cancer cells with target protein expressed to these particles was found to be greatly inhibited (see FIG. 11*b*). The result demonstrates that binding between the cells and the conjugated particles is specific. In addition, a different cell line which expressed little target protein was employed to confirm the binding specificity. Concordant with the blocking peptide results, the binding of the cells with lower target protein expression to the particles with antibody conjugated was much lower when compared to the cancer cells with target protein highly expressed. (see FIG. 11*c*).

Antibody Dosage Effect on the Binding of Cancer Cells with Target Protein Expressed After verification on the ability for the polyacrylic acid (PAA) hydrogel particles of capturing of the cancer cells with target protein expressed specifically, the effect on the dosage of antibody conjugated on the capturing efficiency has been studied. Polyacrylic acid (PAA) hydrogel particles conjugated with different amount of antibody (i.e. 0 μg, 0.2 μg, 1 μg and 5 μg) were incubated with the cancer cells with target protein expressed. The cell-capturing ability and the amount of the antibody used in conjugation showed a positive correlation (see FIG. 12).

The effect on the binding efficiency of the PAA hydrogel particles, which has previously conducted and studied in phosphate buffer saline (PBS), has further been studied in blood medium.

Blood with a 100× dilution was used in the experiment. The blood content is found not to affect the binding efficiency between the conjugated particles and the cancer cells with target protein expressed (see FIG. 13).

Hemoglobin Absorption

Hemoglobin contributed to the red colour in blood including menstrual blood sample. However, menstrual blood is very different from peripheral blood as the red blood cells inside the peripheral blood are intact, and thus they can be easily separated and removed by common technique like centrifugation and therefore, the remaining fluid, known as serum or plasma, is yellowish in color. In menstrual blood, red blood cells were burst, releasing hemoglobin into the solution. The intense red color of hemoglobin in menstrual blood thus cannot be removed by centrifugation or other simple processes, but only by expensive antibody treatment. The intense red colour of hemoglobin will mask the downstream colorimetric measurement and limit the use of menstrual blood for further analysis on site.

As hemoglobin is positively charged, it is important to know if the negatively charged hydrogel could hold the hemoglobin tightly and not releasing the hemoglobin during elution. The relative amount of hemoglobin absorbed by the same weight of cotton and hydrogel using absorbance at OD414 nm are studied. At 37° C., hydrogel absorbed a little bit more hemoglobin than cotton (FIGS. 14*a* and 14*b*) while at 24° C., the absorption were similar in both cotton and hydrogel. Elution buffer was then added to the hydrogel and cotton which already absorbed the hemoglobin. The amount of hemoglobin being eluted out from the cotton is around 3 folds more than that from the hydrogel (FIGS. 14*c* and 14*d*). The results demonstrate that hydrogel is a better material for blood absorption than cotton, which enables downstream detection process using colorimetric method.

Swelling Ratio

The swelling ratio of the polyacrylic acid (PAA) hydrogel particles data is further studied, see FIG. 15. The results demonstrated that the amount of blood absorbed by the particles are within a variation of less than 5%, which implies that the volume of the sample being collected by every particle is similar. The low variation in swelling ratio is beneficial from the angle of manufacturing, as variation from batch to batch of the hydrogel sampling member manufactured will be low.

In another aspect of the present invention, it relates to a sanitary product, such as but not limited to a sanitary pad or napkin, for use in detecting a medical condition of a subject from a body fluid collected or discharged from said subject. The sanitary product comprises a sampling member having one or more polymeric materials such as, but is not limited to, the hydrogel materials as described in the previous embodiments. The sampling member, when arranged to be in contact with the body fluid, collects, captures, stabilizes and/or preserves the constituent biomolecules of the body liquid at the polymeric materials. The sanitary product further comprises a positioning member such as the positioning member of the above described embodiments. Preferably, the positioning member comprises an absorbing material, and that the positioning member is configured to support the sampling member. The sampling member is detachable or removable from the positioning member after the constituent biomolecules are collected for medical diagnosis.

In a further aspect of the present invention, it relates to a method of manufacturing the device for detecting a medical condition of a subject as described above. The method comprises the steps of providing a sampling member have one or more polymeric materials, such as but is not limited to, hydrogel materials as described above. The sampling member, when arranged to be in contact with the body fluid, collects, captures, stabilizes and/or preserves the constituent biomolecules of the body liquid at the polymeric materials. The method further comprises providing a positioning member as previously described which comprises an absorbing material, the positioning member being configured to support the sampling member. Preferably, the positioning member is releasably attachable to and is detachable from a substrate such as, but is not limited to, a sanitary pad or napkin wearable by the subject.

In yet a further aspect of the present invention, it relates to a method of manufacturing an absorbent product, such as, but is not limited to, a sanitary pad or napkin. The method comprises the steps of providing an absorbing layer, and a bottom layer below the absorbing layer; providing the device according to any one or more of the described embodiments at the absorbing layer; and providing an attaching means at the bottom layer for releasably attaching and detaching the absorbent product to and from a clothing of a user.

The present invention is advantageous in that it provides a relatively simple device which can be easily incorporated and/or attached to a sanitary product for collecting and testing menstrual blood for medical diagnosis. The device comprises a sampling member preferably comprising one or more hydrogel materials supported and positioned at or within an absorbing positioning member. The positioning member is preferably configured to comprise two absorbing layers with absorption or penetration rate similar to that of cotton materials for an efficient absorbing of menstrual blood. The device can be attached or inserted in a central portion of the sanitary pad, and preferably, with a transverse axis defining ⅓ of the longitudinal length from the front end of the device, being overlapped with a central transverse axis defining half of the longitudinal length of the sanitary pad. This positioning of the device relative to the sanitary pad allows the most efficient and effective collection of menstrual blood by the device. The hydrogel-based sampling member absorbs the menstrual blood and particularly, collects, captures, stabilizes and/or preserves the constituent biomolecules of the menstrual blood when the blood is absorbed by the sanitary pad. After use and before disposal of the sanitary pad, the device can be removed from the pad and the hydrogel-based sampling member can be detached, collected and then delivered to the laboratory at ambient condition or subjected to on-site detection. This novel invention allows a passive collection of menstrual blood as sample for medical assay using a sanitary pad, which is a feminine hygiene product most commonly used by women for menstruation management, although other types of sanitary products such as tampons or post-surgical napkins shall also be encompassed by the present invention. Moreover, visiting the clinic or testing laboratory in person by the tested subject will no longer be necessary with the present invention, as the menstrual blood can now be preserved and stabilized in the hydrogel sampling member with more than one day to facilitate the subsequent transportation and handling processes. This flexible and efficient collection of blood sample of the present invention is found to significant broaden the use of menstrual blood for disease diagnosis and/or for general health checking. Furthermore, the present invention allows, preserving and stabilizing the constituent biomolecules by preventing the biomolecules from dehydration, as well as inhibiting of bacterial, viral and/or fungal growth, which may otherwise adversely affect the nature and configuration of the biomolecules and thus accuracy of the subsequent assay. The present invention further allows selection of specific biomolecules based on strategic extraction of the biomolecules based on different eluting conditions such as ionic strength, pH and temperature, and/or by coupling or conjugating of biosensing molecules on the hydrogel to further increase accuracy, sensitivity and selectivity of the detection assay. On top of that, additional modifications on the device allow other applications including detection of chemical changes or cells responses. The present invention may further be modified to convent the hydrogel-based sampling member into a bio-sensing platform for an on-site diagnosis. With the current invention, menstrual blood can be collected and tested passively and conveniently.

The present description illustrates the principles of the present invention. It will thus be appreciated that those skilled in the art will be able to devise various arrangements that, although not explicitly described or shown herein, embody the principles of the invention and are included within its spirit and scope.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future, i.e., any elements developed that perform the same function, regardless of structure.

While the invention has been illustrated and described in detail in the drawings and foregoing description, the same is to be considered as illustrative and not restrictive in character, it being understood that only exemplary embodiments have been shown and described and do not limit the scope of the invention in any manner. It can be appreciated that any of the features described herein may be used with any embodiment. The illustrative embodiments are not exclusive of each other or of other embodiments not recited herein. Accordingly, the invention also provides embodiments that comprise combinations of one or more of the illustrative embodiments described above. Modifications and variations of the invention as herein set forth can be made without departing from the spirit and scope thereof, and, therefore, only such limitations should be imposed as are indicated by the appended claims.

In the claims hereof, any element expressed as a means for performing a specified function is intended to encompass any way of performing that function. The invention as defined by such claims resides in the fact that the functionalities provided by the various recited means are combined and brought together in the manner which the claims call for. It is thus regarded that any means that can provide those functionalities are equivalent to those shown herein.

In the claims which follow and in the preceding description of the invention, except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments of the invention.

It is to be understood that, if any prior art publication is referred to herein, such reference does not constitute an admission that the publication forms a part of the common general knowledge in the art.

The invention claimed is:

1. A device for detecting a medical condition of a subject from a menstrual blood sample collected from said subject, the device comprising:

a sampling member comprising one or more crosslinked polymeric materials, the sampling member, when arranged to be in contact with the menstrual blood sample, collects and retains constituent biomolecules of the menstrual blood sample at the crosslinked polymeric materials to allow retention, preservation and stabilization of the collected biomolecules; wherein the one or more crosslinked polymeric materials comprise a synthetic crosslinked hydrophilic polyacrylic acid hydrogel material configured to absorb the menstrual blood sample and swell to retain water within the hydrogel to thereby prevent dehydration of the collected biomolecules for at least 48 hours at ambient condition;

wherein the crosslinked hydrogel material is porous with pore sizes of about 20 μm to retain only specific biomolecules and to exclude microbes based on size to provide a microbial inhibitory effect; and wherein the synthetic crosslinked hydrophilic polyacrylic acid hydrogel material is negatively charged to inhibit microbial adhesion and growth; and a positioning member comprising an absorbing material, the positioning member being configured to support the sampling member;

wherein the positioning member is releasably attachable to a substrate wearable by the subject;

wherein the crosslinked polymeric materials are coupled, attached or conjugated with one or more biosensing molecules to thereby enable detection of targeted biomolecules specific to the biosensing molecules; and wherein the sampling member is configured such that, after collection, one or more types of the retained biomolecules are selectively elutable from the crosslinked polymeric materials by contacting the sampling member with an elution buffer having one or more predetermined conditions comprising pH, ionic strength, temperature, and/or an applied electric field.

2. The device according to claim 1, wherein the one or more crosslinked polymeric materials are provided in the form of particles; with particle sizes ranged from about 1 mm to about 3 mm.

3. The device according to claim 1, wherein the biomolecules are collected and stabilized by the crosslinked structure of the one or more crosslinked hydrogel polymeric materials.

4. The device according to claim 1, wherein the positioning member comprises at least two layers of absorbing material, with the sampling member being arranged therebetween.

5. The device according to claim 4, wherein the positioning member is configured in the form of a pocket with at least one opening for receiving the sampling member.

6. The device according to claim 1, wherein the positioning member comprises one or more materials selected from a group consisting of: cotton, rayon, polyester, non-woven gauze and/or silk.

7. The device according to claim 4, wherein the sampling member comprises one or more sampling units planarly arranged between the at least two layers of the positioning member.

8. The device according to claim 7, wherein the one or more sampling units are configured in one or more of 2-dimensional shapes and 3-dimensional shapes; wherein the 2-dimensional shapes comprise one or more shapes of a square, a rectangle, a triangle, a circle, a strap, a polygon, and an irregular shape, and the 3-dimensional shapes comprise one or more of a cuboid, a sphere, a pyramid, a prism, a cylinder, and a polyhedron.

9. The device according to claim 1, further comprising a detaching means for detaching the device from the substrate wearable by the subject; wherein the detaching means comprises an elongated structure extending away from the positioning member.

10. The device according to claim 1, wherein the one or more biosensing molecules are selected from a group consisting of: nucleic acids, proteins, antigens, antibodies, enzymes, cells, cellular structures, biomimetic materials, functional particles, metals and small molecules.

11. The device according to claim 1, wherein the biomolecules are selected from a group consisting of cells, nucleic acids, proteins, antigens, antibodies, enzymes.

12. The device according to claim 1, wherein the substrate wearable by the subject comprises an absorbent product.

13. An absorbent product for detecting a medical condition of a subject from a menstrual blood sample collected from said subject, the absorbent product comprising:

an absorbing layer, a bottom layer arranged below the absorbing layer, and the device according to claim 1 arranged at the absorbing layer.

14. The absorbent product according to claim 13, further comprising a top layer above the absorbing layer and define a cavity with the absorbing layer for receiving the device; wherein the top layer is configured with an opening for receiving the device into the cavity.

15. The absorbent product according to claim 13, wherein at least part of the absorbing layer is perforated for detaching the device from said absorbing layer.

16. A method of manufacturing the device for detecting a medical condition of a subject from a menstrual blood sample collected from said subject according to claim 1, comprising the steps of:

providing a sampling member comprising one or more crosslinked polymeric materials, the sampling member, when arranged to be in contact with a body fluid of a subject, collects, retains and stabilises constituent biomolecules of the body fluid at the polymeric materials; wherein the one or more crosslinked polymeric materials comprise a synthetic crosslinked hydrophilic polyacrylic acid hydrogel material configured to absorb the menstrual blood sample and swell to retain water within the hydrogel to thereby prevent dehydration of the collected biomolecules for at least 48 hours at ambient condition;

wherein the crosslinked hydrogel material is porous with pore sizes of about 20 μm to retain only specific biomolecules and to exclude microbes based on size to provide a microbial inhibitory effect; and wherein the synthetic crosslinked hydrophilic polyacrylic acid hydrogel material is negatively charged to inhibit microbial adhesion and growth; and providing a positioning member comprising an absorbing material, the positioning member being configured to support the sampling member;

wherein the positioning member is releasably attachable to a substrate wearable by the subject;

wherein the crosslinked polymeric materials are coupled, attached or conjugated with one or more biosensing molecules to thereby enable detection of targeted biomolecules specific to the biosensing molecules, and wherein the sampling member is configured such that, after collection, one or more types of the retained biomolecules are selectively elutable from the crosslinked polymeric materials by contacting the sampling member with an elution buffer having one or more predetermined conditions comprising pH, ionic strength, temperature, and/or an applied electric field.

* * * * *